(12) United States Patent
Chen et al.

(10) Patent No.: US 9,603,795 B2
(45) Date of Patent: Mar. 28, 2017

(54) COMPOSITE FOR PREPARING A TRANSDERMAL DELIVERY DEVICE AND METHOD FOR SYNTHESIZING THE COMPOSITE THEREOF

(71) Applicant: City University of Hong Kong, Kowloon (HK)

(72) Inventors: Wei Chen, Kowloon (HK); Xianfeng Chen, New Territories (HK)

(73) Assignee: City University of Hong Kong, Hong Kong (HK)

( * ) Notice: Subject to any disclaimer, the term of this patent is extended or adjusted under 35 U.S.C. 154(b) by 0 days.

(21) Appl. No.: 14/220,272

(22) Filed: Mar. 20, 2014

(65) Prior Publication Data
US 2015/0265714 A1     Sep. 24, 2015

(51) Int. Cl.
*A61K 47/48*     (2006.01)
*A61K 9/00*      (2006.01)

(52) U.S. Cl.
CPC ...... *A61K 9/0021* (2013.01); *A61K 47/48969* (2013.01)

(58) Field of Classification Search
None
See application file for complete search history.

(56) References Cited

U.S. PATENT DOCUMENTS

2008/0269685 A1* 10/2008 Singh .................. A61K 9/0021
                                                         604/173

* cited by examiner

*Primary Examiner* — Brian Gulledge
(74) *Attorney, Agent, or Firm* — Renner Kenner Greive Bobak Taylor & Weber (57) ABSTRACT

A composite for preparing a transdermal delivery device and a method for synthesizing the composite thereof comprising at least one polymer and at least one macrocyclic molecule, wherein the at least one polymer and the at least one macrocyclic molecule are adapted to form a complex.

16 Claims, 7 Drawing Sheets

COMPOSITE FOR PREPARING A TRANSDERMAL DELIVERY DEVICE AND METHOD FOR SYNTHESIZING THE COMPOSITE THEREOF

TECHNICAL FIELD

The present invention relates to a composite, and a composite for preparing a transdermal delivery device, and particularly, although not exclusively to polyvinylpyrrolidone-cyclodextrin (PVP-CD) inclusion complexes for use in microneedle arrays.

BACKGROUND

Compared with conventional needle and syringe intramuscular and subcutaneous injection, transdermal delivery by microneedle arrays possesses many advantages such as minimal pain and infection, high drug efficacy, and potential of self-administration.

Polymers are often used for fabricating dissolving microneedle arrays for transdermal delivery. In this approach, drugs are usually incorporated in the interior of dissolvable polymer microneedles. Once the microneedles pierce skin, the polymers will dissolve and rapidly release drugs within desired skin layers. Compared with commonly used silicon and metal microneedles, polymer microneedle arrays are cheap to manufacture, safe to use and having no remaining sharp waste post application. However, polymer microneedles may have weak mechanical properties and strong water absorption properties in humidified environment which hampers the mechanical strength of such microneedles.

The composite of the present invention is arranged to ameliorate the above problems or, more generally, to provide an improved composite for preparing a transdermal delivery device.

SUMMARY OF THE INVENTION

According to a first aspect of the present invention, there is provided a composite for preparing a transdermal delivery device, comprising at least one polymer and at least one macrocyclic molecule, wherein the at least one polymer and the at least one macrocyclic molecule are adapted to form a complex.

In one embodiment of the first aspect, the at least one polymer comprises polyvinylpyrrolidone (PVP), PVP copolymer, PVP derivatives and a mixture thereof.

In one embodiment of the first aspect, the PVP copolymer and PVP derivatives comprise poly(vinyl pyrrolidone/vinylacetate), poly(vinylpyrrolidone/vinylcaprolactam), Poly(1-vinylpyrrolidone-co-2-dimethylaminoethyl methacrylate), poly(1-vinylpyrrolidone-co-styrene), and poly(1-vinylpyrrolidone)-graft-(1-triacontene).

In one embodiment of the first aspect, the at least one polymer is selected from a group consisting of poly(N-isopropylacrylamide) (PNIPAM), polyacrylamide (PAM), poly(vinyl alcohol) (PVA), poly(ethylene glycol) (PEG), poly(ethylene oxide) (PEO), polymers comprising PNIPAM, PAM, PVA, PEG, or PEO, and a mixture thereof.

In one embodiment of the first aspect, the polymers comprising PNIPAM, PAM, PVA, PEG, or PEO comprises poly(ethylene glycol)-block-poly(propylene glycol)-block-poly(ethylene glycol), poly(ethylene oxide)-poly(propylene oxide)-poly(ethylene oxide), or poly(vinyl alcohol-co-ethylene)ethylene In one embodiment of the first aspect, the at least one polymer comprises polyelectrolytes selected from the group of polystyrenesulfonate, poly(allylamine hydrochloride), poly(acrylic acid) (PAA) and a mixture thereof.

In one embodiment of the first aspect, the polyvinylpyrrolidone is of a molecular weight ranged from about 2,000 to about 1,500,000 g/mol.

In one embodiment of the first aspect, the polyvinylpyrrolidone is of a molecular weight of about 10,000 g/mol.

In one embodiment of the first aspect, the polyvinylpyrrolidone is of a molecular weight of about 58,000 g/mol.

In one embodiment of the first aspect, the marcocyclic molecule comprises cyclodextrin (CD) or derivative thereof.

In one embodiment of the first aspect, the cyclodextrin comprises α-cyclodextrin (α-CD), β-cyclodextrin (β-CD), γ-cyclodextrin (γ-CD) or a mixture thereof.

In one embodiment of the first aspect, the cyclodextrin derivatives comprise acyl-cyclodextrin, tosyl-cyclodextrin, alkyl-cyclodextrin, hydroxyalkyl-cyclodextrin, carboxyl-cyclodextrin, dimethyl-cyclodextrin, trimethyl-cyclodextrin, randomly methylated-cyclodextrin, glucosyl-cyclodextrin, maltosyl-cyclodextrin, sulfoalkyl-cyclodextrin, aminocyclodextrin, cyclodextrin phosphate or a mixture thereof.

In one embodiment of the first aspect, the hydroxyalkyl-cyclodextrin comprises hydroxypropyl-β-cyclodextrin.

In one embodiment of the first aspect, the alkyl-cyclodextrin comprises dimethyl-β-cyclodextrin.

In one embodiment of the first aspect, the marcocyclic molecule comprises cucurbituril, calixarene, pillararene or a mixture thereof.

In one embodiment of the first aspect, the complex comprises an inclusion complex.

In one embodiment of the first aspect, the transdermal delivery complex is adapted to carry therapeutics of low water solubility.

In one embodiment of the first aspect, the transdermal delivery complex is adapted to release therapeutics in a controlled manner.

In one embodiment of the first aspect, the transdermal delivery device comprises at least one micro-needle.

In one embodiment of the first aspect, the transdermal delivery device comprises at least one microneedle disposed on a substrate.

In one embodiment of the first aspect, the transdermal delivery device is in the form of a patch.

According to a second aspect of the present invention, there is provided a method of synthesizing a composite for preparing transdermal delivery device, comprising steps of: dissolving at least one polymer and at least one marcocyclic molecule in a solvent to form a solution; and evaporating the solvent to form a complex of the at least one polymer and the at least one marcocyclic molecule.

In one embodiment of the second aspect, the method further comprising a step of mixing the solution prior to the evaporating step.

In one embodiment of the second aspect, the mixing step comprises at least one of ultra-sound sonicating and physical stirring.

In one embodiment of the second aspect, the at least one polymer is selected from a group consisting of polyvinylpyrrolidone (PVP), or PVP copolymer, PVP derivatives and a mixture thereof.

In one embodiment of the second aspect, the polyvinylpyrrolidone is of a molecular weight ranged from about 2,000 to about 1,500,000 g/mol.

In one embodiment of the second aspect, the at least one marcocyclic molecule comprises cyclodextrin (CD) or derivative thereof.

In one embodiment of the second aspect, the cyclodextrin comprises α-cyclodextrin (α-CD), β-cyclodextrin (β-CD), γ-cyclodextrin (γ-CD) or a mixture thereof.

In one embodiment of the second aspect, the cyclodextrin derivative comprises acyl-cyclodextrin, tosyl-cyclodextrin, alkyl-cyclodextrin, hydroxyalkyl-cyclodextrin, carboyxl-cyclodextrin, dimethyl-cyclodextrin, trimethyl-cyclodextrin, randomly methylated-cyclodextrin, glucosyl-cyclodextrin, maltosyl-cyclodextrin, sulfoalkyl-cyclodextrin, aminocyclodextrin, cyclodextrin phosphate or a mixture thereof.

In one embodiment of the second aspect, the hydroxyalkyl-cyclodextrin comprises hydroxypropyl-β-cyclodextrin.

In one embodiment of the second aspect, the alkyl-cyclodextrin comprises dimethyl-β-cyclodextrin.

In one embodiment of the second aspect, the marcocyclic molecule comprises cucurbituril, calixarene, pillararene or a mixture thereof.

In one embodiment of the second aspect, the at least one polymer and the at least one marcocyclic molecule is in a mole ratio of about 1:10 to about 50:1.

In one embodiment of the second aspect, the complex comprises an inclusion complex.

According to a third aspect of the present invention, there is provided a device for transdermal delivery of therapeutics, comprising a plurality of micro-needles prepared by a composite in accordance with the first aspect of the present invention.

In one embodiment of the third aspect, the therapeutics comprise drug that is substantially insoluble in water.

In one embodiment of the third aspect, the drug comprises benexate, dexamethasone, iodine, nicotine, omeprazole, piroxicam, cisapride, hydrocortisone, indomethacin, mitomycin, itraconazole, voriconazole, chloramphenicol, 5-FU or a mixture thereof. Preferably, the drug also comprises aromatic rings.

In one embodiment of the third aspect, the drug is arranged to form a drug complex with the at least one macrocyclic molecule in the composite.

According to a fourth aspect of the present invention, there is provided a device for transdermal delivery of therapeutics, comprising a plurality of micro-needles prepared by a composite synthesized by a method in accordance with the second aspect of the present invention.

According to a fifth aspect of the present invention, there is provided a composite comprising at least one polymer and at least one macrocyclic molecule, wherein the at least one polymer and the at least one macrocyclic molecule are adapted to form a complex.

In one embodiment of the fifth aspect, the at least one polymer is selected from a group consisting of polyvinylpyrrolidone (PVP), PVP copolymer, PVP derivatives and a mixture thereof; and wherein the marcocyclic molecule comprises cyclodextrin (CD) or derivative thereof.

In one embodiment of the fifth aspect, the at least one polymer and the at least one marcocyclic molecule is in a mole ratio of about 1:10 to about 50:1.

In one embodiment of the fifth aspect, the complex comprises an inclusion complex.

BRIEF DESCRIPTION OF THE DRAWINGS

Embodiments of the present invention will now be described, by way of example, with reference to the accompanying drawings in which:

FIG. 6 shows the SEM images of various PVP and PVP-CD microneedle arrays in accordance with one embodiment of the present invention, in which:

FIG. 6(a) is the image of a PVP58 microneedle array,

FIG. 6(b) is the image of a PVP58-HP-β-CD-11 microneedle array,

FIG. 6(c) is the image of a PVP10 microneedle array, and

FIG. 6(d) is the image of a PVP10-HP-β-CD-11 microneedle array; and

FIG. 7 shows the SEM images of a pig skin and the microneedle arrays after application of various PVP and PVP-CD microneedle arrays in accordance with one embodiment of the present invention to the pig skin, in which:

FIG. 7(a) is a pig skin image after application of a PVP58 (PVP58 represents the PVP with molecular weight of 58,000) microneedle array, FIG. 7(b) is a pig skin image after application of a PVP58-HP-β-CD-11 (PVP58-HP-β-CD-11 represents weight ratio of PVP10 to HP-β-CD is 1:1) microneedle array, FIG. 7(c) is an image of the PVP58 microneedle array after application to the pig skin, and FIG. 7(d) is an image of the PVP10-HP-β-CD-11 microneedle array after application to the pig skin.

DETAILED DESCRIPTION OF THE INVENTION

Polymer such as polyvinylpyrrolidone (PVP) shows excellent biocompatibility and water solubility and therefore is often used as a main component for temporary skin covers and wound dressing. In addition, these polymers are also used in the pharmaceutical industry as coating agents, polymeric membranes, and materials for controlled drug release. Although PVP has been reported to make microneedles, its poor mechanical properties and strong water absorption properties seriously limit the practical usage, especially for low molecular weight PVP.

On the other hand, macrocyclic molecules or cyclic oligomers such as cyclodextrin (CD) manufactured from starch, has been used in pharmaceutical industry for drug coating and delivery. Of different types of CDs, β-CD is the most accessible and the lowest-priced type. Oral administration of β-CD is minimally irritating and has many advantages including very small amounts (1-2%) being absorbed in the upper intestinal tract, no metabolism happening in the upper intestinal tract, and being able to be metabolized by bacteria in caecum and colon.

The inventor of the present invention has devised through experiments and trials that macrocyclic molecules such as CD or derivatives thereof can form inclusion complexes (host-guest complexes) with a very wide range of solid, liquid and gaseous compounds by molecular complexation. The hydrophobic cavity of macrocyclic molecules such as CD molecules may provide a microenvironment for appropriately sized non-polar moieties to enter and form inclusion complexes, with no covalent bonding between the macrocyclic molecules and moieties. Replacement of water in the cavity by hydrophobic guest molecules may lead to reduction of enthalpy, which leads to host-guest complexes formation, in which the complexes can be formed in either solution or solid state. The inventor of the present invention has also devised that being locked or caged within the cavity of the macrocyclic molecules such as CD may give rise to beneficial modifications of the guest molecules including enhanced solubility, anti-oxidation under visible or UV light or heat, controllability of volatility and sublimation, physical isolation of incompatible compounds, masking off unpleasant odours and controlled drug release.

Figure 1:
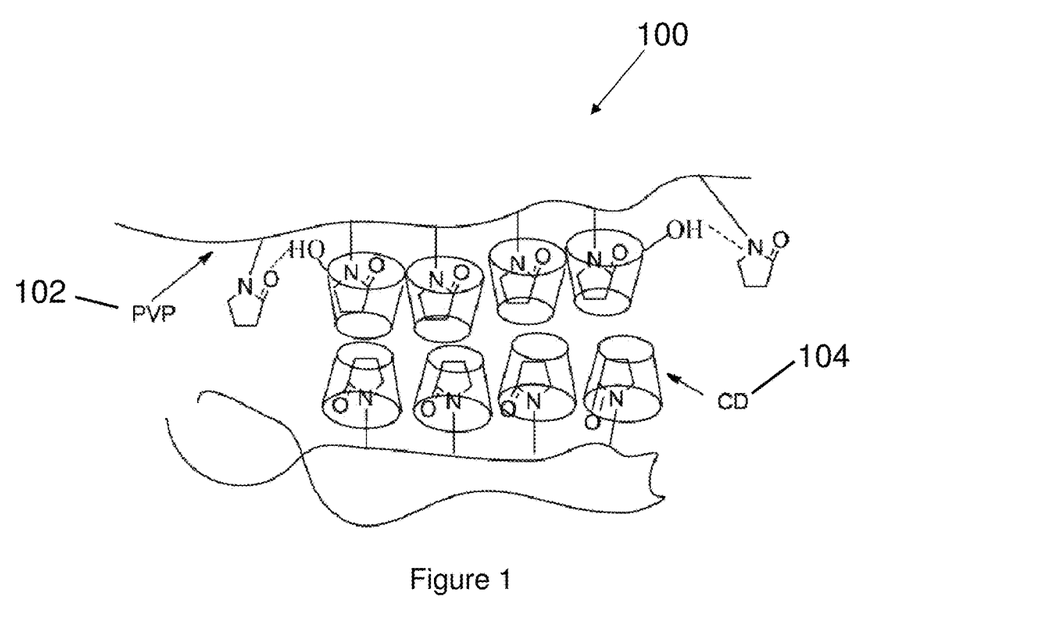
FIG. 1 is a schematic of a PVP-CD complex in accordance with one embodiment of the present invention.

Referring to FIG. 1, there is provided a composite 100 for preparing a transdermal delivery device, comprising at least one polymer and at least one macrocyclic molecule, wherein the at least one polymer and the at least one macrocyclic molecule are adapted to form a complex. In the example of FIG. 1, the polymer comprises polyvinylpyrrolidone (PVP) 102 whilst the macrocyclic molecule comprises cyclodextrin (CD) 104.

Preferably, the polymer used in the composite of the present invention comprises not only polyvinylpyrrolidone (PVP), but also or PVP copolymer (such as graft polymer, block polymer, modified polymer), PVP derivatives and a mixture thereof. For example, the PVP copolymer and PVP derivatives may comprise poly(vinyl pyrrolidone/vinylacetate), poly(vinylpyrrolidone/vinylcaprolactam), poly(1-vinylpyrrolidone-co-2-dimethylaminoethyl methacrylate), poly(1-vinylpyrrolidone-co-styrene), or poly(1-vinylpyrrolidone)-graft-(1-triacontene).

In some embodiments, the polymer used in the composite of the present invention may be selected from a group consisting of poly(N-isopropylacrylamide) (PNIPAM), polyacrylamide (PAM), poly(vinyl alcohol) (PVA), poly (ethylene glycol) (PEG), poly(ethylene oxide) (PEO), polymers comprising PVA, PEG, PEO or PVP, and a mixture thereof. Examples of polymers comprising PVA, PEG, PEO or PVP include poly(ethylene glycol)-block-poly(propylene glycol)-block-poly(ethylene glycol), poly(ethylene oxide)-poly(propylene oxide)-poly(ethylene oxide), or poly(vinyl alcohol-co-ethylene)ethylene.

In some embodiments, the polymer used in the composite of the present invention may be polyelectrolytes such as polystyrenesulfonate, poly(allylamine hydrochloride), poly (acrylic acid) (PAA) and a mixture thereof.

In the embodiments of which PVP is used, the polyvinylpyrrolidone is preferably of a molecular weight ranged from about 2,000 to about 1,500,000 g/mol. In one exemplary embodiment, the polyvinylpyrrolidone is of a molecular weight of about 10,000 g/mol or about 58,000 g/mol.

Preferably, the macrocyclic molecule used in the composite of the present invention comprises cyclodextrin (CD) or derivative thereof, or alternatively, cucurbituril, calixarene, pillararene or a mixture thereof. In one embodiment, the cyclodextrin used may comprise α-cyclodextrin (α-CD), β-cyclodextrin (β-CD), γ-cyclodextrin (γ-CD) or a mixture thereof whereas the cyclodextrin derivatives used may comprise acyl-cyclodextrin, tosyl-cyclodextrin, alkyl-cyclodextrin, hydroxyalkyl-cyclodextrin, carboxyl-cyclodextrin, dimethyl-cyclodextrin, trimethyl-cyclodextrin, randomly methylated-cyclodextrin, glucosyl-cyclodextrin, maltosyl-cyclodextrin, sulfoalkyl-cyclodextrin, aminocyclodextrin, cyclodextrin phosphate or a mixture thereof. Optionally, the hydroxyalkyl-cyclodextrin comprises hydroxypropyl-β-cyclodextrin and the alkyl-cyclodextrin comprises dimethyl-β-cyclodextrin. Preferably, the complex formed by the at least one polymer and the at least one macrocyclic molecule comprises an inclusion complex.

The transdermal delivery complex in the present invention is adapted to, for example, carry therapeutics or drugs that is water insoluble or with low water solubility, or release the therapeutics or drugs in a controlled manner. Examples of the drug that may be used in the present invention includes drug that contains aromatic ring, as well as benexate, dexamethasone, iodine, nicotine, omeprazole, piroxicam, cisapride, hydrocortisone, indomethacin, mitomycin, itraconazole, voriconazole, chloramphenicol, 5-FU or a mixture thereof. Preferably, the drugs is arranged to form a drug complex with the macrocyclic molecule in the transdermal delivery complex and these drugs may be water soluble or water insoluble.

In some embodiments, the transdermal delivery device comprises at least one micro-needle. The micro-needles may be arranged in an array and/or may be disposed on a substrate. Preferably, the transdermal delivery device is in the form of a patch.

Examples of the transdermal delivery complexes of the present invention formed by adding either one of two types of CD (Hydroxypropyl-β-Cyclodextrin (HP-β-CD) and Dimethyl-β-Cyclodextrin (DIME-β-CD)) into either one of PVP of two different molecular weights (Mn=58000 (named as PVP58) and Mn=10000 (named as PVP10)) are provided below.

A skilled person would readily appreciate that the complexes described below are only meant to be exemplary and should not be considered limiting. Other chemicals with similar functional groups arranged to perform the same functions or with similar chemical properties may also be used in the present invention without deviating from the scope of the present invention.

EXPERIMENTAL SECTION

Raw Materials

PVP58, PVP10, sodium chloride, potassium chloride, potassium acetate, HP-β-CD and DIME-β-CD from Sigma Aldrich® and poly(dimethylsiloxane) (PDMS, SYL-GALD® 184) from Dow-Corning® were used. All of the materials were used raw without further treatment.

Inclusion Complexes Preparation

In the present examples, non-stoichiometric PVP58 and HP-β-CD inclusion complexes were prepared according to the following procedures. Firstly, 50 mg of PVP58 and 50 mg of HP-β-CD were dissolved in 1 ml of water followed by 30 minutes of sonication and 1 day of stirring. Then, the composite was placed at room temperature for two days until the water had been evaporated. After that, the sample was placed into containers containing various saturated salt solutions for relative humidity (RH) control. The product was named as PVP58-HP-β-CD-11 ("11" indicates that the weight ratio of PVP to HP-β-CD was 1:1). Other samples, including PVP58-HP-β-CD-51, PVP10-HP-β-CD-11, PVP10-HP-β-CD-51, PVP58-DIME-β-CD-11, PVP58-DIME-β-CD-51, PVP10-DIME-β-CD-11, and PVP10-DIME-β-CD-51, were prepared with the same process. PVP58 and PVP10 film were prepared with the similar process except without adding CD.

Microneedle Arrays Preparation

In the present examples, the complexes microneedle arrays were prepared according to the following. A mould was first prepared by applying PDMS base and crosslinking agent with a volume ratio of 10:1 to a silicon master microneedle array followed by curing at room temperature for two days. To make polymer microneedles, PVP or PVP-CD aqueous solution was cast onto the PDMS mould. The solution was forced to the microneedle cavity in the mould by a vacuum environment. After drying at room temperature for two days, high concentration PVP58 or PVP10 solution (50 wt %) was cast to form the base of the microneedle patch.

Water Absorption at Various Relative Humidity Conditions

PVP-CD complexes were firstly placed in a dry desiccator for two days to allow all samples to have equivalent conditions before water absorption measurement. Then the samples were stored at ambient temperature under various controlled relative humidity (RH) conditions by using saturated salt solutions of potassium acetate (23% RH), sodium chloride (75% RH), and potassium chloride (85% RH). Subsequently, water absorption was determined using a gravimetric method by drying samples in a vacuum oven at elevated temperature of 50° C. until a constant weight was achieved. The water content was calculated as the weight loss after drying in relative to the weight of the sample before temperature elevation.

Differential Scanning Calorimetry (DSC)

The glass transition temperatures ($T_g$) of samples were tested by DSC (TA Q1000) under nitrogen atmosphere. The first cycles were performed from about 50° C. to about 230° C. at a temperature increase Rate of about 10° C./min and then maintained at 230° C. for 3 minutes to erase any previous thermal history. After that, the samples were cooled down to 50° C. at a rate of 30° C./min. Finally, the samples were reheated to 230° C. at a rate of 10° C./min. The registered changes on the calorimetric curves were evaluated.

Fourier Transform Infrared Spectroscopy (FTIR)

Fourier transform infrared spectroscopy (Spectrum 100 PerkinElmer) spectra of samples were obtained using KBr disk for 40 scans with a resolution of 2 $cm^{-1}$ in the range of 4000 to 400 $cm^{-1}$.

Hardness and Young's Modulus Test

PVP and PVP-CD films were prepared by drying the corresponding solutions on glass slides. A micro-indentation with a Vickers diamond indenter (Fischerscope® HM2000, Fischer®, Germany) was used to measure the Young's modulus and hardness of the films under 70% RH. Under a load level of 10 mN, the mean values of hardness and Young's modulus were derived from load versus indentation depth curves. At least 5 indentations were performed for each sample.

Scanning Electron Microscopy (SEM)

SEM images were taken with a Philips®, XL30 Environmental scanning electron microscope (ESEM) with a voltage of 10 kV. To obtain high quality images of polymer microneedle patches, gold coating was applied to the patches.

Microneedle Array Application to Pig Skin

In the present examples, a pig skin penetration test was performed with the various PVP and PVP-CD complexes microneedle arrays. The experiment was performed with the following procedures. Firstly, pig ears were obtained from the local abattoir and thoroughly cleaned. The ventral side of the pig ear was then lightly shaved and rinsed. The skin was then stored at −20° C. before usage. Before microneedle array penetration test, the ventral skin (epidermis and dermis) was separated from the cartilage by tweezers and scalpel. The ventral skin was then stretched on a substrate and the fabricated complexes microneedle arrays (PVP58, PVP58-HP-β-CD-11) were applied to the skin with a spring-based applicator. Immediately after the application, the microneedle arrays were removed from the skin. The treated area was excised with biopsy and fixed in 5 ml 4% formaldehyde in 0.1 M phosphate buffered saline overnight. Subsequently, the tissue was washed with 0.1 M phosphate buffered saline. The morphology of the microneedle penetrated pig skin and the used microneedle arrays were observed with ESEM (Philips®, XL30).

Results and Discussion

FTIR Spectra of PVP, CD and PVP-CD Complexes

Figure 2A:
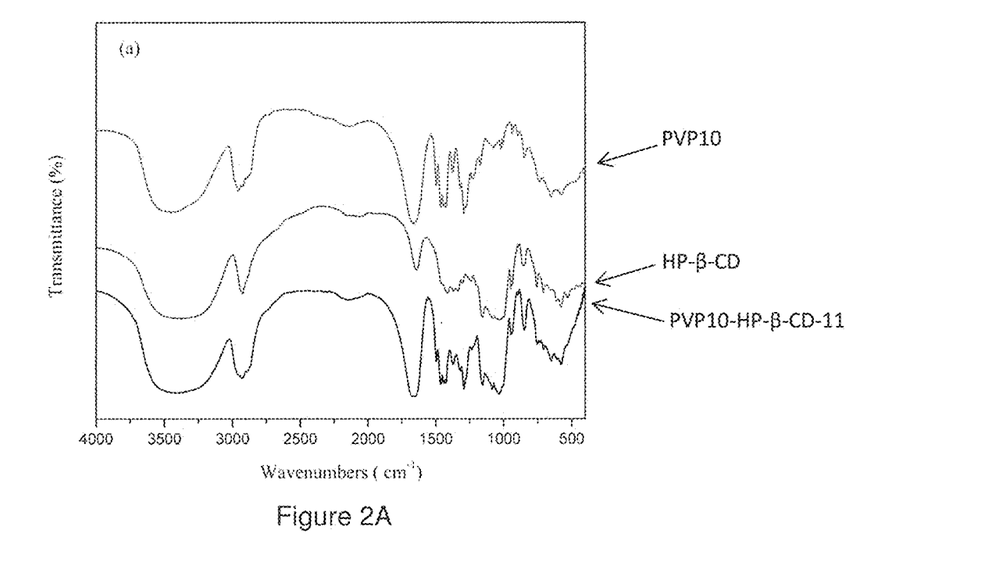
FIG. 2A shows the Fourier transform infrared (FTIR) spectra of PVP10, HP-β-CD, and PVP10-HP-β-CD-11 complexes (PVP10 represents the PVP with molecular weight of 10,000; PVP10-HP-β-CD-11 represents weight ratio of PVP10 to HP-β-CD is 1:1) in accordance with one embodiment of the present invention.

In the present examples, the formation of PVP-CD inclusion complexes was first confirmed by FTIR, which is a very useful tool to prove the existence of both guest and host molecules in complexes. FIG. 2A shows the FTIR spectra of PVP58, HP-β-CD, and PVP58-HP-β-CD-11 inclusion complexes. The peak at 3466 $cm^{-1}$ is attributed to the hydroxyl group of water (although the sample was totally dried before FTIR test), which proves PVP quickly absorbs water. This peak overlaps with the hydroxyl group of HP-β-CD. The peaks at 3370 $cm^{-1}$, 2928 $cm^{-1}$, 1157 $cm^{-1}$, and 1029 $cm^{-1}$ correspond to the symmetric and antisymmetric stretching of —OH, —CH2, C—C, and bending vibration of O—H, respectively. The peaks at 2962 $cm^{-1}$, 2933 $cm^{-1}$, and 2904 $cm^{-1}$ correspond to the stretching of C—H in the PVP chain.

For HP-β-CD, the peak at 2929 $cm^{-1}$ is the stretching vibration of —CH3 and —CH2. The peaks at 1156 $cm^{-1}$ and 1079 $cm^{-1}$ are the stretching bending vibrations of C—O—C and C—O—H, respectively. The peaks at 946 $cm^{-1}$ and 856 $cm^{-1}$ correspond to α-1,4 skeletal vibrations and a pyranoside bond, respectively. At 757 $cm^{-1}$, there is a sugar ring breathing vibration peak. The peak at 707 $cm^{-1}$ is a ring vibration peak.

Figure 2B:
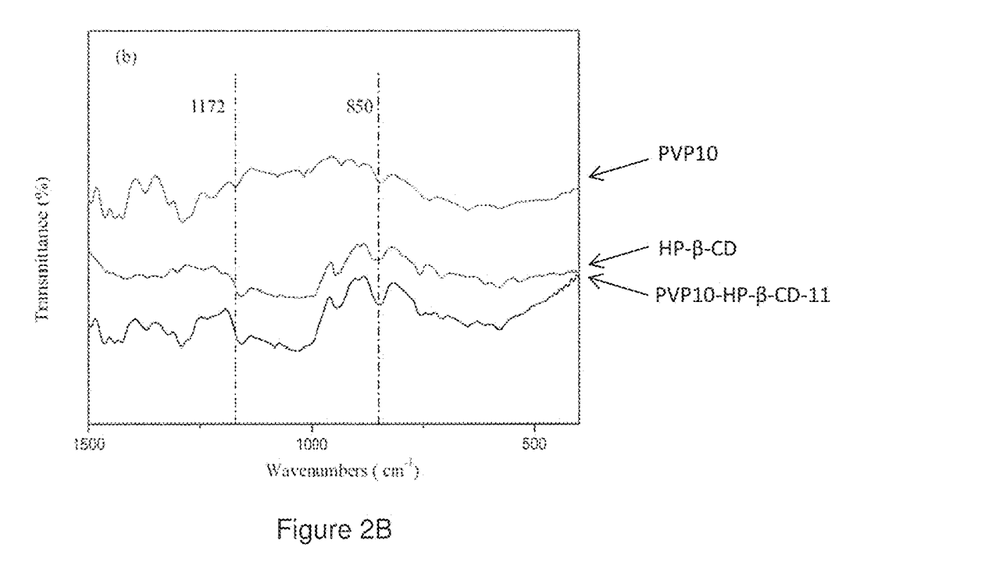
FIG. 2B shows the Fourier transform infrared (FTIR) spectra of PVP10, HP-β-CD, and PVP10-HP-β-CD-11 complexes (PVP10 represents the PVP with molecular weight of 10,000; PVP10-HP-β-CD-11 represents weight ratio of PVP10 to HP-β-CD is 1:1) in accordance with one embodiment of the present invention.

The frequency movements of PVP-HP-β-CD inclusion complexes are shown in FIG. 2B. The axial and angular bending C—C(=O) of PVP is located at 1172 $cm^{-1}$. After the formation of the complexes, this peak shifts 16 $cm^{-1}$ to 1156 $cm^{-1}$. In addition, the peak of the out of plane bending CH2 of PVP shifts from 850 $cm^{-1}$ to 847 $cm^{-1}$ in the complexes. Overall, the shifts of the two peaks clearly confirm the formation of the PVP-HP-β-CD inclusion complexes and this is likely caused by the microenvironment change of the CD cavity due to the formation of the inclusion complexes. Preferably, in the present examples, the increase and decrease of the wavenumbers are dependent on the host-guest interactions. In the present examples of the invention, the non-stoichiometric PVP-CD inclusion complexes are heterogeneous. Parts of N-vinylpyrrolidone are included in the β-CD cavity and parts are dangling. The hydrogen bonding between the hydroxyl group of the outer cavity of CD and N-vinylpyrrolidone constrains the mobility of PVP chain, which corresponds to the decrease in the FTIR absorption wavenumbers of stretching and bending vibration of C—H, C=O and C—N.

Water Absorption of PVP and PVP-CD Complexes

Water is a plasticizer of amorphous materials that often leads to degradation of their mechanical and thermal properties. The inventor of the present invention has devised through experiments and trials (with FTIR measurements) that water molecules can be bonded to C=O, and C—N groups in PVP. Furthermore, the inventor of the present invention has also devised through experiments and trials (using a Fourier transform Raman spectrum) that showed the change of the properties of PVP via water absorption are not only due to hydrogen bonding, but also a result of the plasticizing effect of water. Water molecules distribute uniformly throughout PVP at a concentration of 0.5%, but become remarkably heterogeneous at a higher content. Besides moderately strong hydrogen bonding, extra water molecules are in free state, which acts as a plasticizing agent. Therefore, reduction of water absorption by PVP will be beneficial to maintain mechanical and thermal properties.

Figure 3A:
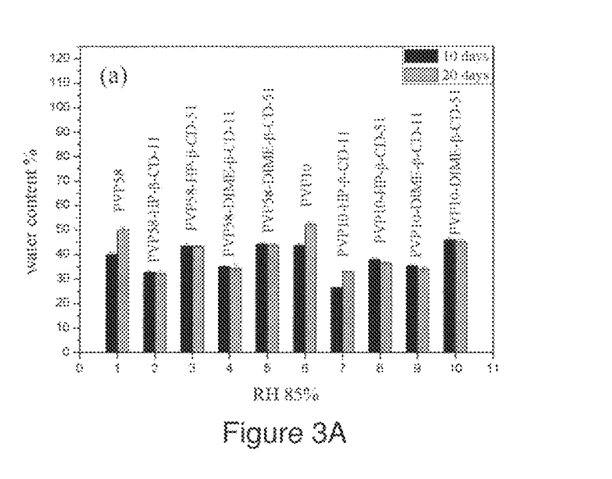
FIG. 3A shows the water absorption properties of various PVP and PVP-CD complexes under different relative humidity (RH) percentages in accordance with one embodiment of the present invention.
Figure 3B:
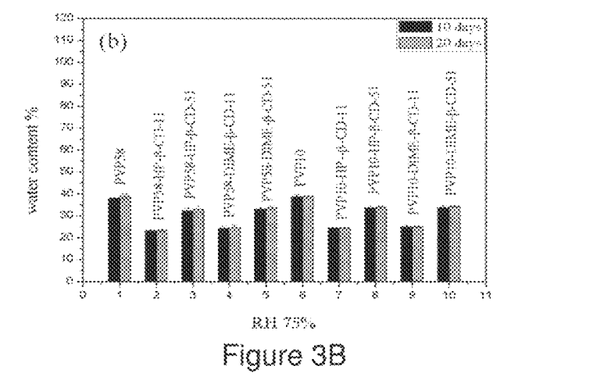
FIG. 3B shows the water absorption properties of various PVP and PVP-CD complexes under different relative humidity (RH) percentages in accordance with one embodiment of the present invention.
Figure 3C:
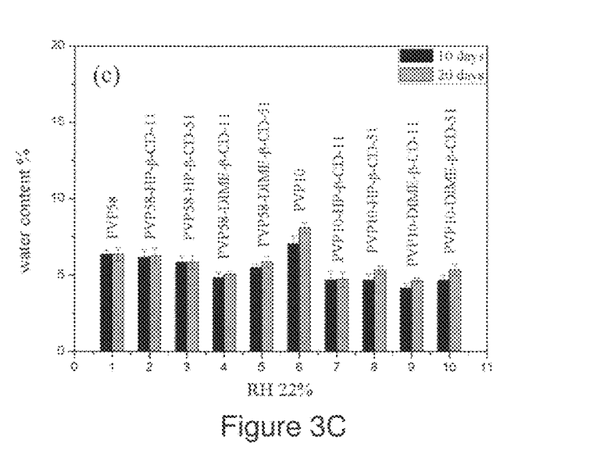
FIG. 3C shows the water absorption properties of various PVP and PVP-CD complexes under different relative humidity (RH) percentages in accordance with one embodiment of the present invention.

The water absorption of various PVP-CD complexes under different RH conditions is shown in FIGS. 3A-3C. As shown in FIGS. 3A-3C, under different RHs, the water absorption capacity varies. At low RH of 22%, the water absorption is low. Adding CD to PVP can reduce PVP58 and PVP10 water absorption by only around 1 and 3 wt %, respectively. If the relative decrease in water absorption is calculated, for PVP10, the water absorption decreases from 8% to 4.9% after 20 days exposure to RH 22% environment. This means that the relative decrease of water absorption is about 40%. When RH increases to 75% and 85%, the effect of CD incorporation is more obvious because higher RH leads to increased water absorption of PVP. If the water absorption of PVP and PVP-CD inclusion complexes are compared, the following can be observed. The water absorption was 50 wt % and 32 wt % for PVP10 and PVP10-CD complexes, respectively, after 20 days exposure to RH 85% environment. This indicates a relative 36% decrease in water absorption. For PVP58, the effect is about the same. At RH75%, for PVP58, the water absorption drops from 37 wt % to 23% after complexes formation, which suggests about 38% relative decrease. Overall, the data show that after formation of PVP-CD complexes, water absorption can decrease about 36-40% at different RHs.

Different PVP-CD ratios were investigated in the above experiments (through various trials) and the results clearly indicate that the ratio of 1:1 worked best in terms of decreasing water absorption of PVP. However, in other examples, the PVP-CD ratio could be up in the range of 1:10 to 50:1 without deviating from the scope of the invention.

In addition, it can also be found that, at a high RH of 85%, the water absorption of PVP dramatically increases if the time exposure to the environment extends from 10 to 20 days. In comparison, for the PVP-CD complexes, longer time exposure to the environment usually does not lead to increased water absorption. The above result suggests that the formation of PVP-CD complexes is good for long term storage.

Glass Transition Temperatures of PVP and PVP-CD Complexes

TABLE 1

Glass transition temperature of PVP and PVP-CD complexes

| Sample | $T_g$ (° C.) |
| --- | --- |
| PVP58 | 160 |
| PVP58-HP-β-CD-11 | 199 |
| PVP58-HP-β-CD-51 | 176 |
| PVP58-DIME-β-CD-11 | 210 |
| PVP58-DIME-β-CD-51 | 158 |
| PVP10 | 128 |
| PVP10-HP-β-CD-11 | 165 |
| PVP10-HP-β-CD-51 | 136 |
| PVP10-DIME-β-CD-11 | 155 |
| PVP10-DIME-β-CD-51 | 135 |

Figure 4:
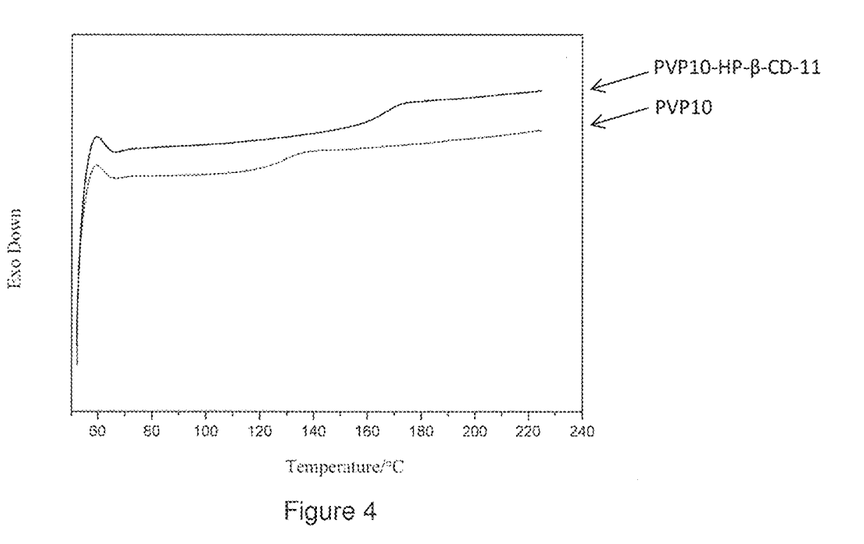
FIG. 4 shows a plot of the differential scanning calorimetry (DSC) curves of PVP and PVP10-β-CD-11 complexes in accordance with one embodiment of the present invention.

FIG. 4 shows the DSC curves of PVP58 and PVP58-HP-β-CD-11 inclusion complexes. Compared with PVP, it can be observed that the $T_g$ of PVP58-HP-β-CD-11 is greatly increased from 160° C. to 199° C., increasing by 39° C. Referring to Table 1, it is shown that after formation of PVP-CD complexes, the glass temperatures increased for various compounds. This is likely due to the fact that non-stoichimetric polymer-CD inclusion complexes often show different physical properties from the pure one. For example, nylon-6 CD inclusion complexes may have higher $T_m$ and non-stoichimetric PMMA-CD inclusion complexes may show higher $T_g$ than pure PMMA. In addition, N-s-PCL-α-CD inclusion complexes may display shape memory effects depending on the coverage of inclusions and the storage modulus may be significantly higher than that of the pure PCL.

During glass transition, an amorphous polymer undergoes secondary phase change, changing from a brittle solid state, to an elastic rubbery state, reflecting increased chain mobility. As N-vinylpyrrolidone is in the inner cavity of CD, the chain mobility is limited and the dangling chain showed brush structure interacting with the hydroxyl group outside the cavity of CD, both of which contribute to tighter and more ordered structure.

Mechanical Properties of PVP and PVP-CD Complexes

Figure 5A:
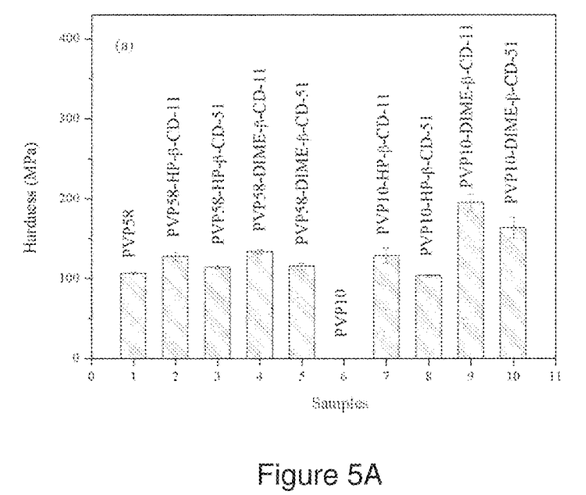
FIG. 5A shows the hardness of various PVP and PVP-CD complexes in accordance with one embodiment of the present invention.
Figure 5B:
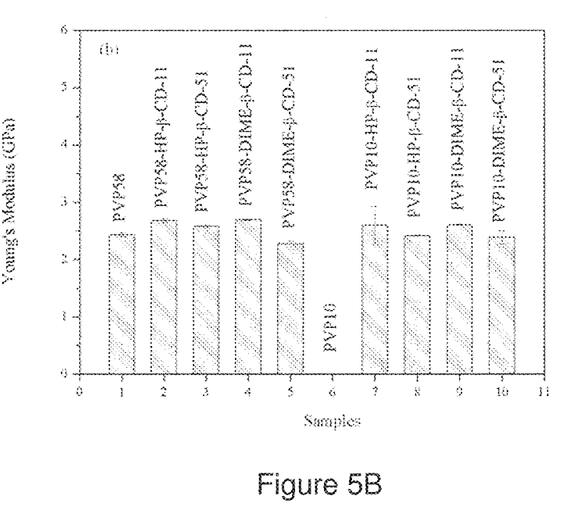
FIG. 5B shows the Young's modulus of various PVP and PVP-CD complexes in accordance with one embodiment of the present invention.

The micro indentation test results of the exemplary PVP and PVP-CD complexes of the present invention are shown in FIGS. 5A and 5B. It can be seen from the Figures that, with CD, the Vickers hardness (HV) and Young's modulus increase. In FIGS. 5A and 5B, the hardness and Young's modulus of PVP58-HP-β-CD-11 are 127.7 MPa and 2.681 GPa, respectively, which increased 19.6% and 10.2% in comparison with those of PVP58 with hardness of 106.8 MPa and Young's modulus of 2.433 GPa, respectively. The hardness and Young's modulus of PVP58-DIME-β-CD-11 showed similar results.

For PVP10, the strengthening effect is more obvious. The hardness and Young's modulus of PVP10 could not be tested as the samples quickly absorb high amount of water and became viscous before measurement. In contrast, after adding CD to PVP10, it can be clearly seen that the hardness and Young's modulus of PVP-CD were close to those of PVP58. For PVP10-HP-β-CD-11 and PVP10-DIME-β-CD-11, the hardness and Young's modulus were 128.7 MPa, 2.598 GPa and 194.8 MPa, 2.611 GPa, respectively, which is even close to PVP58. These results showed that the incorporation of CD may enhance mechanical properties, especially for low molecular weight PVP.

Low molecular weight PVP generally has faster water solubility than high molecular weight ones. For microneedles, faster dissolving rates can be very important for vaccine delivery. As indicated by the data in FIGS. 5A and 5B, low molecular weight PVP has poor mechanical properties, which restrains its application. Through by adding CD to PVP10 to form complexes in accordance with the present invention, this problem can be alleviated. Overall, it can be concluded that the addition of CD may significantly increase the mechanical strength of PVP.

By comparing the effect of the ratio of PVP to CD and the type of CD on the mechanical properties of the complexes, it can be found that the ratio plays an important role while the type of the tested CD does not have much influence.

The function of CD in the present invention has been explained above. The CD cavity is occupied by the N-vinylpyrrolidone molecules. This host-guest effect constrains the mobility of the polymer chain. Non-stoichimetric CD allows left PVP chains to be still dangling without being encompassed by CD molecules. In this example, the hydrogen bonds formed between left N-vinylpyrrolidone and CD molecules will decrease the possibility of water interaction to N-vinylpyrrolidone and this is not related to outspace of CD.

Fabrication of PVP and PVP-CD Microneedle Arrays

In the present invention, the PVP and PVP-CD complexes are applied to fabricating microneedle arrays and the morphology of the fabricated microneedle arrays are examined. In this experiment, all microneedle arrays fabricated underwent the same manufacturing and processing procedures before scanning electron microscopy observation.

Figure 6:
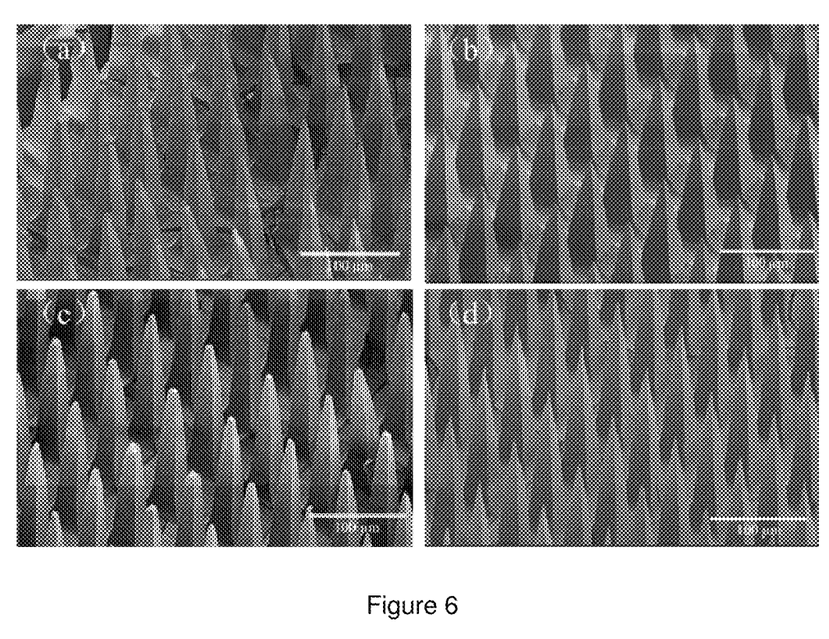

The morphology of microneedles, particularly the radius of the tips, is often one of the important factors which may affect the microneedles penetration to skin. As shown in FIG. 6, the morphology of the tips of the PVP and PVP-CD microneedles has great differences. Specifically, the PVP-CD microneedles have much sharper tips, which allows them easily penetration to the skin. In addition, this kind of microneedles has very low number of cracks on the base. In contrast, many PVP58 microneedles tips are even flat and bent, base has cracks. With reference to FIG. 6, this phenomenon is perhaps more serious for PVP10 microneedles. In these examples, the cracks and blunt tips were mainly caused by water absorption.

PVP and PVP-CD Microneedle Arrays Penetration to Skin

Figure 7:
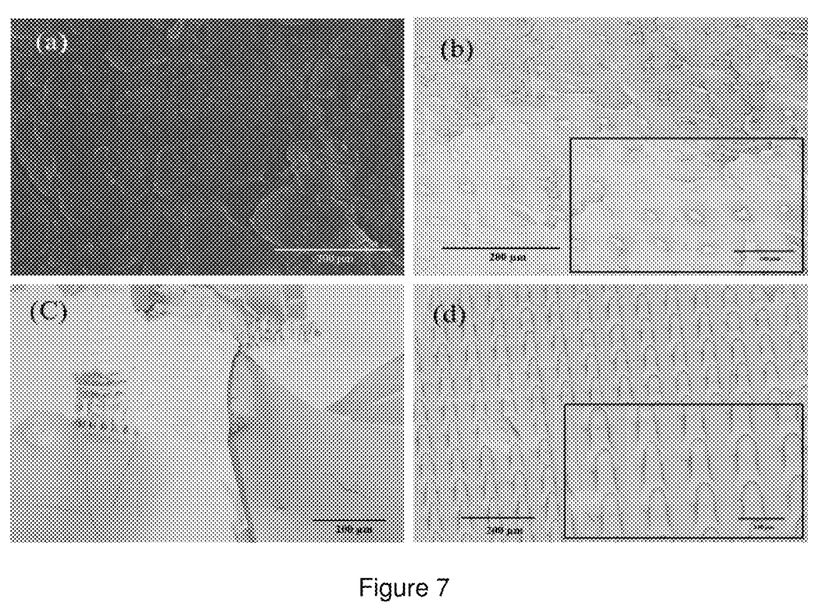

In the present examples, the exemplary PVP and PVP-CD microneedles were applied to pig skin to investigate whether the incorporation of CD may improve the microneedle penetration. To perform the test, PVP and PVP-CD microneedle arrays were applied to pig skin separately and the morphology of the treated skin surface and the used microneedle arrays were characterized with ESEM. The SEM images are shown in FIG. 7. From FIG. 7(a), it can be seen that the PVP microneedles were not able to pierce the stratum corneum of the pig skin. In great contrast, FIG. 7(b) clearly shows that the PVP-CD microneedles successfully penetrate into the skin and ordered holes are created due to the penetration of the microneedles to the skin. Because the skin was not completely dehydrated before SEM characterization, the skin may shrink or distort due to water loss during the SEM observation. For PVP microneedle arrays, once applied to the skin, the patches were smashed to many small pieces. Most of the microneedle arrays disappeared after application. For the several remained microneedles as shown in FIG. 7(c), it was observed that some of them were bent possibly due to the fact that these microneedles were not mechanically strong enough to pierce the stratum corneum of the pig skin. In comparison, all of the microneedles of the PVP-CD patches were remained after the application as shown in FIG. 7(d). However, the tips of the microneedles were dissolved after being penetrated into the pig skin within the very short period of penetration time (about 1 second). Overall, the results clearly indicate that the PVP-CD microneedles can successfully penetrate into the pig skin and rapidly start to dissolve while the pure PVP microneedles with the same geometry are not capable of piercing the stratum corneum of the skin.

CONCLUSION

Based on the above disclosure, a person skilled in the art would readily appreciate that the composite of the present invention may be applied to different applications. For example, the composites may be arranged to aid transdermal drug/vaccine delivery. Alternatively, the composites may be applied to prepare transdermal delivery devices such as microneedles for improving the mechanical properties and water absorption properties (reducing the water absorption) of the microneedles. In this way, the microneedles may be arranged to deliver water insoluble or minimally soluble drugs. The composites of the present invention may also facilitate controlled drug release.

The composites of the present invention provide a number of unique advantages. Particularly, the composites of the present invention may be arranged such that the dissolving microneedles prepared from the composites are mechanically more robust yet still fast-dissolving. Also, the dissolving polymer microneedles with the composites may absorb less water and may thus able to maintain their mechanical properties. Furthermore, the transdermal delivery complex may be used for deliver water insoluble or minimally soluble drugs. Other advantages of the present invention in terms of structure, function, cost, and operation effectiveness will become apparent to a person skilled in the art with reference to the above description.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Any reference to prior art contained herein is not to be taken as an admission that the information is common general knowledge, unless otherwise indicated.

The invention claimed is:

1. A composite for preparing a transdermal delivery device, comprising at least one polymer and at least one macrocyclic molecule at a weight ratio of 1:1, wherein the at least one polymer is selected from polyvinylpyrrolidone (PVP), PVP copolymers, PVP derivatives, and a mixture thereof, and the at least one macrocyclic molecule is selected from cyclodextrin and derivatives thereof; and the at least one polymer and the at least one macrocyclic molecule are adapted to form an inclusion complex.

2. The composite according to claim 1, wherein the PVP copolymer and PVP derivative comprise poly(vinyl pyrrolidone/vinylacetate), poly(vinylpyrrolidone/vinylcaprolactam), poly(1-vinylpyrrolidone-co-2-dimethylaminoethyl methacrylate), poly(1-vinylpyrrolidone-co-styrene), and poly(1-vinylpyrrolidone)-graft-(1-triacontene).

3. The composite according to claim 1, wherein the polyvinylpyrrolidone is of a molecular weight ranged from about 2,000 to about 1,500,000 g/mol.

4. The composite according to claim 1, wherein the polyvinylpyrrolidone is of a molecular weight of about 10,000 g/mol.

5. The composite according to claim 1, wherein the polyvinylpyrrolidone is of a molecular weight of about 58,000 g/mol.

6. The composite according to claim 1, wherein the cyclodextrin comprises α-cyclodextrin (α-CD), β-cyclodextrin (β-CD), y-cyclodextrin (y-CD) or a mixture thereof.

7. The composite according to claim 1, wherein the cyclodextrin derivatives comprise acyl-cyclodextrin, tosyl-cyclodextrin, alkyl-cyclodextrin, hydroxyalkyl-cyclodextrin, carboxyl-cyclodextrin, dimethyl-cyclodextrin, trimethyl-cyclodextrin, randomly methylated-cyclodextrin, glucosyl-cyclodextrin, maltosyl-cyclodextrin, sulfoalkyl-cyclodextrin, aminocyclodextrin, cyclodextrin phosphate or a mixture thereof.

8. The composite according to claim 7, wherein the hydroxyalkyl-cyclodextrin comprises hydroxypropyl-β-cyclodextrin.

9. The composite according to claim 7, wherein the alkyl-cyclodextrin comprises dimethyl-β-cyclodextrin.

10. The composite according to claim 1, wherein the inclusion complex is adapted to carry therapeutics of low water solubility.

11. The composite according to claim 1, wherein the inclusion complex is adapted to release therapeutics in a controlled manner.

12. The composite according to claim 1, wherein the transdermal delivery device comprises at least one microneedle.

13. The composite according to claim 1, wherein the transdermal delivery device comprises at least one microneedle disposed on a substrate.

14. The composite according to claim 1, wherein the transdermal delivery device is in the form of a patch.

15. A composite comprising at least one polymer and at least one macrocyclic molecule with a weight ratio of 1:1, wherein the at least one polymer is selected from polyvinylpyrrolidone (PVP), PVP copolymer, PVP derivative and a mixture thereof, and the at least one macrocyclic molecule is selected from cyclodextrin and a derivative thereof; the at least one polymer and the at least one macrocyclic molecule are adapted to form an inclusion complex.

16. The composite according to claim 15, wherein the at least one polymer and the at least one macrocyclic molecule is in a mole ratio of about 1:10 to about 50:1.

* * * * *